United States Patent [19]

Cavallotti et al.

[11] Patent Number: 5,703,242
[45] Date of Patent: Dec. 30, 1997

[54] PREPARATION OF SOLUTIONS OF IMIDO-ALKANCARBOXYLIC ACIDS SUITABLE FOR PEROXIDATION PROCESSES

[75] Inventors: Claudio Cavallotti; Gilberto Nucida; Claudio Troglia, all of Milan, Italy

[73] Assignee: Ausimont, S.p.A., Italy

[21] Appl. No.: 777,699

[22] Filed: Dec. 20, 1996

[30] Foreign Application Priority Data

Dec. 21, 1995 [IT] Italy .................. MI95A2718 U

[51] Int. Cl.$^6$ .................................................. C07D 209/48
[52] U.S. Cl. .................. 548/473; 548/476; 568/558; 568/561
[58] Field of Search ................ 548/479, 473, 548/476; 568/558, 561; 210/634

[56] References Cited

U.S. PATENT DOCUMENTS

| 5,061,807 | 10/1991 | Gethoffer | 548/473 |
| 5,208,340 | 5/1993 | Cavallotti | 548/479 |
| 5,310,934 | 5/1994 | Cavallotti | 548/479 |
| 5,470,988 | 11/1995 | Jaekel | 548/479 |
| 5,487,818 | 1/1996 | Cavallotti | 203/41 |

FOREIGN PATENT DOCUMENTS

| 0 349 940 A1 | 1/1990 | European Pat. Off. | 548/473 |
| 0 490 409 A1 | 6/1992 | European Pat. Off. | 548/473 |
| 0 670 821 A1 | 7/1994 | European Pat. Off. | 548/473 |

OTHER PUBLICATIONS

J.H. Billman et al. "Amino Acids. V. Phthalyl Derivatives" J. Am. Chem. Soc., vol. 70; 1473-74 (1948).

B. Taub et al., "ε-Imido Esters. I. The Course of the Reaction between Phthalic Anhydride and Caprolactam" J. Org. Chem. Soc., vol. 24; 2062-63 (1959).

R. Stuart Tipson, "N,N-Phthaloyl-L-glutamic Acid and Some Derivatives", J. Org. Chem. Soc., vol. 21; 1353-57 (1956).

B. Taub et al., "ε-Imido Esters. The Reaction between Anhydrides and ε-Caprolactam" J. Chem. Eng. Data, vol. 10, 399-401 (1965).

*Primary Examiner*—Ernest G. Therkorn
*Attorney, Agent, or Firm*—Finnegan, Henderson, Farabow, Garrett & Dunner, L.L.P.

[57] ABSTRACT

Purification process of imido-alkancaboxylic acids from contaminants represented by acid-carboxylic, lactam or aminoacids and water comprising:

A) Preparation of the imido-alkancarboxylic acid precursor by reaction of an anhydride a1) or the corresponding acids, with an aminoacid b1) with water; or a1) with a lactam b2) and water; at temperatures comprised between 100° and 250° C., under pressure of an inert gas from 1 to 30 bar, for reaction times from 2 to 20 hours; wherein the ratio by moles between a1/(b1 or b2)/water is comprised between 1/1.05-1.1/0.5-2.5; optional addition of water such that it is at least, of 2 moles for mole of a1);

B) discharge of the precursor obtained in phase A) in a solvent immiscible with water;

C) separation of the aqueous phases from the organic phase;

D) recovery of the organic phase for the successive peroxidation reaction.

13 Claims, No Drawings

PREPARATION OF SOLUTIONS OF IMIDO-ALKANCARBOXYLIC ACIDS SUITABLE FOR PEROXIDATION PROCESSES

The present invention relates to a process for preparing imido-alkancarboxylic acids which are known precursors for preparing the corresponding peroxycarboxylic acids.

The latter compounds are utilized as bleaching agents in detergent formulations or as main components of disinfectant or oxidizing compositions. These products combine good bleaching properties with a good storage stability.

The preparation of these imido-alkancarboxylic acids is well known in the literature and considers, for instance for the phthalimidoalkancarboxylic acid class, a sum or condensation among phthalic anhydride, or phthalic acid, and aminoacids or lactams in absence or in presence of water, with a pressure from 1 to 30 bar, at temperatures ranging from 100° to 250° C. and with reaction times from 5 to 20 hours. See for instance: J. Am. Chem. Soc., Vol. 70, 1473 (1948); J. Org. Chem. Soc., Vol. 24, 2062 (1959); J. Org. Chem., Vol. 21, 1353 (1956); J. Chem. Eng. Data, Vol. 10, 399 (1965).

In EP patent 349,940 (corresponding to U.S. Pat. No. 5,061,807 a process is described for preparing precursors obtained by reeaction of an anhydride and a lactam, or aminoacid, in the presence of water, under the conditions in general indicated above.

The obtained product contains however a high amount of contaminants such as carboxylic acid, lactam or aminoacid and/or water.

By the processes known in the art the imidoalkancarboxylic acids (indicated here generically by PAC), generally contain impurities in high amounts deriving from the reactants used. In the case of phthalimidoalkancarboxylic acids, the usual impurities are the following (% by weight):

1.5–10% of phthalic acid,
0.5–10% of lactam,
1.0–20% of water.

See for instance European patent application EP 607,821.

In general contaminants are those deriving from the reactants as indicated hereinafter by a1) (anhydrides or acids), b1) (aminoacids), b2) (lactams), c1) (water).

The presence of said contaminants agents leads to drawbacks since in the subsequent oxidation step for the preparation of the corresponding percarboxylic acids in the presence of hydrogen peroxide and of a strong acid some inconveniences occur. Even if the precursor is obtained with high yields of 97–98%, the impurities mentioned above give the following drawbacks for instance in the case of the class of phthalimidoalkancarboxylic acids.

The phthalic acid, because of its poor solubility in the solvents often utilized in peroxidation, causes the product precipitation in the solvent solutions of the peroxidation process, with consequent plugging of pumps, filters, etc. Besides, such acid, in oxidizing environment, gives rise to peroxydic by-products, by taking away $H_2O_2$ to the system with consequent yield decrease.

Moreover the by-products of the phthalic acid formed in the peroxidation process negatively influence the storage stability of the obtained peracid (here generically indicated by PAP).

This leads to additional processes of the peracid phlegmatisation so that this maintains a good storage stability.

Also the other mentioned contaminants, often not very soluble in the solvents utilized in the peroxidation phase, must be removed in order to have high yields in the peracid.

Water, for instance, if not removed from the precursor, implies a remarkable increase of the amount of sulphuric acid to be used for the synthesis, with consequent problems of elimination of the refluent acids of the process and consequent increase of the production costs.

For the caprolactam the same inconveniences indicated above occur if it is present in high amounts.

Purification processes of the precursor to remove the impurities indicated above are therefore known.

See for instance EP 607,821 wherein the phthalimidoalkanacarboxylic acid prepared according to the processes of the art is brought to melting and the melt is maintained for a prolonged time at such a temperature that the contaminants are substantially removed from the melt in vapour phase and only successively the purified melted product is cooled. In the melting phase it is utilized an inert gas flow such as argon or nitrogen and/or reduced pressures comprised between 0.1 and 300 millibar to make the removal of the impurities easier. The treatment times are generally of 5 hours or lower if it is operated at higher temperatures or with higher vacuum degrees.

By means of this melting and evaporation process, purified precursor can be obtained which it would not be possible to get with the known purification processes, such as filtering or phase separation for the removal of the indicated contaminants.

The Applicant has surprisingly and unexpectedly found a simplified process to obtain imido-alkancarboxylic acids precursors with the amounts of the above mentioned contaminants to such an extent as not to cause inconveniences either in the peroxidation phase, or in the storage phase of the final peracid.

Object of the present invention is therefore a purification process of imido-alkancarboxylic acids from the contaminants represented by carboxylic acid, lactam or aminoacids and water comprising:

A) preparation of the imido-alkancarboxylic acid by reaction of:
   a1) an anhydride of formula

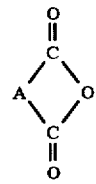

or the corresponding acids, with
   b1) an aminoacid of formula

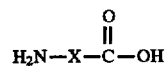

with
   c1) water; or
   a1) with
   b2) a lactam of general formula

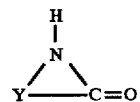

with
   c1) water; at temperatures comprised betweeen 100° C. and 250° C., under pressure of an inert gas from 1 to 30 bar, for reaction times from 2 to 20 hours;

wherein A indicates a group of formula

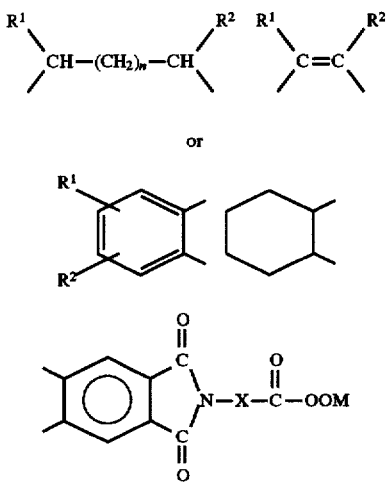

n is an integer 0, 1 or 2,

R$^1$ is hydrogen, chlorine, bromine, alkyl C$_1$–C$_{20}$, alkenyl C$_2$–C$_{20}$, aryl or alkylaryl, R$^2$ is hydrogen, chlorine, bromine or a group of formula —SO$_3$M, —CO$_2$M, —CO$_3$M, —OSO$_3$M, M indicates hydrogen, an alkaline metal or ammonium ion or the equivalent of an alkaline-earth metal ion and X indicates alkylene C$_1$–C$_{19}$ or arylene;

Y is=X and is preferably an alkylene C$_3$–C$_{19}$;

wherein the ratio by moles between a1/(b1 or b2)/c1 is comprised between 1/1.0–1.2/0.5–3;

B) discharge of the precursor obtained in phase A) in a solvent immiscible with water;

C) separation of the aqueous phases from the organic phase;

D) recovery of the organic phase for the successive peroxidation reaction.

Preferably the ratio by moles a1/ (b1 or b2)/c1) is comprised between 1/1.05–1.1/0.5–2.5, more preferably between 1/1.05–1.1/1–2.

The preferred compounds of type b) are those of class b2).

Among the compounds of class a1) the following anhydrides or the corresponding acids can be mentioned: succinic, glutaric, maleic, trimellitic, phthalic, pyromellitic and alkyl- or alkenyl-succinic anhydride. Phthalic anhydride or pthalic acid are preferably used.

Among the compounds of class b1) it can be mentioned: omega-aminobutyric acid, omega-aminovalerianic, omega-amino-caproic and omega-aminolauric acid.

Among the compounds of class b2) can be mentioned as the preferred ones: gamma-pyrrolidone, delta-piperidone, epsilon-caprolactam and omega-laurolactam, epsilon-caprolatam (CPL) is particularly preferred.

Preferably in phase A) the temperature is comprised between 130° C. and 180° C. and the pressure between 4 and 8 bar.

In phase B) any solvent immiscible with water can be utilized, such as for instance chlorobenzene, dichloroethane, CH$_2$Cl$_2$ and CHCl$_3$, solvents such as CH$_2$Cl$_2$ and CHCl$_3$ and CHCl$_3$ are preferably utilized, more preferably CH$_2$Cl$_2$.

These solvents, indeed, as described in EP patent 490,409, are the most suitable to carry out the subsequent peroxidation operation.

Moreover it has been unexpectedly found that if one operates in reaction A) with an amount of water equal to 2 moles per mole of compound a1), preferably phthalic anhydride, and when compound b) is preferably of class b2), more preferably caprolactam, an eutectic of the precursor (PAC) with water is formed. In case the preferred compounds are used the amount of water in the eutectic being of about 12% by weight; the melting point of the eutectic being about 78° C.

The formation of the eutectic brings remarkable advantages to the process of the invention since it allows to discharge the melted mass of the PAC obtained in phase A) in the solvent of phase B) at temperatures ranging from 78°–95° C., preferably 78°–90° C., for the case of the eutectic indicated as an example, by using the preferred compounds.

The amount of solvent in phase B) is such that the solution obtained is utilizable directly in the successive peroxidic synthesis phase if the chosen solvent utilized is fitted to this process. In this way, since the temperature of the eutectic is lower than the melting temperature of the PAC purified according to the methods of the art, for instance according to EP 607,821, which results to be 107°–108° C., it is obtained a lower loss of the solvent and a final temperature of the solution got in phase B) which is lower than the boiling temperature of the solvent.

As an example reference has been made here to the preferred solvent CH$_2$Cl$_2$ as solvent of phase B).

Indeed the process of successive peroxidation of the precursor (PAC) to peracid (PAP) is preferably carried out according to the process indicated in EP patent 490,409.

If the amount of water used in phase A) is lower than 2 moles per 1 mole of phthalic anhydride, water can be added also at the end of phase A) so that the amount of final water is equal to at least 2 moles, preferably higher, with respect to 1 mole of phthalic anhydride, to have the formation of the eutectic and to obtain therefore the advantages indicated above in phase B).

Tests carried out by the Applicant have shown that when in the peroxidation process (to PAP), for instance according to the process indicated in EP patent 490,409, a PAC purified according to the patent EP 607,821 is utilized, yields in final product of 94.35% by weight are obtained. Starting from PAC obtained according to the process of the present invention, by utilizing as reactants a1) phthalic anhydride, b2) caprolactam, c1) water, the amounts of impurities indicated above present according to EP patent 607,821 are extremely reduced, practically absent.

In the peroxidation process molar ratios PAC/H$_2$O$_2$/H$_2$SO$_4$=1/1.5/1.28, have been utilized, by using a reaction temperature of 35° C. and a reaction time of 1 hour.

The PAC obtained according to the process of the present invention after phase D (see examples 2–3) leads to conversions into PAP of the same type of those indicated above, and the final organic solution obtained after phase D) appears clear and it easily separates from the aqueous layer.

The PAP obtained by utilizing said PAC results stockable without using phlegmatising agents.

Moreover in the preferred embodiment according to the present invention, the solutions obtained in phase D) are already prepared with the most suitable solvent for the peroxidation itself, when CH$_2$Cl$_2$ is used as solvent, and moreover in the desired concentration, about 20% by weight of PAC.

As alreeady said in the preferred embodiment according to the present invention the preparation of said ready-to-use solution of PAC in CH$_2$Cl$_2$ is easy thanks to the surprising property of the PAC precursor, preferably of the pthalimido-hexanoic acid, to form an eutectic with H$_2$O (about 12% weight/weight) which has melting point of 78° C., considerably lower than the PAC melting point of 107° C.

This allows to introduce the melted mass obtained by the synthesis of PAC in phase A), at a temperature of 78°–90° C., directly in phase B) in the solvent amount, preferably $CH_2Cl_2$, required for the peroxidic synthesis, obtaining in the so formed solution a temperature lower than the boiling temperature of the solvent itself.

A benefit in energy efficiency terms derives therefrom.

The following examples are given for illustrative purposes and are not limitative of the scope of present invention.

EXAMPLE 1 (comparative)—Phase A)

7.4 g of phthalic anhydride, 5.65 of caprolactam and 1.8 g of $H_2O$ (molar ratios between the components 1:1:2) are introduced in a 30 ml steel autoclave equipped with a stirrer. Vacuum is carried out in the equipment and the system is brought then to atmospheric pressure with nitrogen. Such cycle is repeated three times. Then the inner pressure is brought to 1 bar with nitrogen. It is heated to 160° C. and the mixture of the reactants is stirred by keeping it at this temperature for 6 hours, at the pressure of 6 bar.

The system is cooled at 85°–90° C. and the pressure of the reactor is then reduced up to the atmospheric value.

All the reaction mixture is then discharged in acetonitrile or dioxane, and the content in PAC, phthalic acid and caprolactam is determined by HPLC analysis and the content in $H_2O$ of the mixture itself by Karl Fischer.

14.78 g of mixture with the following composition (% by weight) were thus obtained:

| PAC | 86% |
|---|---|
| Caprolactam | 1.06% |
| Water | 11.7% |
| Phthalic acid | 1.24% |

The conversion was of 97.4% by weight.

EXAMPLE 2

74 g of phthalic anhydride, 59.5 g of caprolactam and 18 g of $H_2O$ with molar ratio of the components 1:1.05:2, are condensed in a 300 ml autoclave according to the modalities described in Example 1 (phase A)).

At the end of the reaction, the melted mass, eutectic PAC/$H_2O$=149 g, is slowly discharged at 85° C. into 520 g of $CH_2Cl_2$ maintained under stirring in a 1000 ml separatory funnel (phase B)).

Phases C) and D).

After 3 hours of staying, (at 30°–35° C.), an aqueous surface layer is separated from the organic solution, which can be easily removed from the organic solution by means of the separatory funnel.

The obtained organic solution (PAC in $CH_2Cl_2$), ready to be sent to peroxidation, contains:

| PAC | 19.92% by weight |
|---|---|
| Caprolactam | 0.14% by weight |
| $H_2O$ | 0.38% by weight |
| Phthalic acid | 0.009% by weight | the remaining part 100% is formed by $CH_2Cl_2$.

EXAMPLE 3

74 g of phthalic anahydride, 59.5 g of caprolactam and 19 g of $H_2O$ are condensed in a 300 ml autoclave according to the modalities described in example 1, but utilizing a pressure of 7 bar, then proceeding as described in example 2.

The PAC organic solution in $CH_2Cl_2$, separated by the aqueous phase (Phase D)) has the following composition:

| PAC | 19.9% by weight |
|---|---|
| Caprolactam | 0.14% by weight |
| $H_2O$ | 0.42% (2.06% on PAC) by weight |
| Phthalic acid | 0.013% by weight | the remaining part 100% is formed by $CH_2Cl_2$.

The residual content of water present in the PAC chloro-containing solution is determined via Karl Fischer.

EXAMPLE 4 (comparative)

74 g of phthalic anhydride, 56.5 g of caprolacetam and 18 g of $H_2O$ are condensed in a 300 ml autoclave, as in example 1-Phase A).

The obtained mixture (g 148) is discharged in 520 g of $CH_2Cl_2$ (Phase B)). After 12 hours of staying, the solution still shows a strong emulsibility and a remarkable turbidity due to product in suspension (phthalic acid). It is not possible to clearly separate the aqueous phase from the organic one, not even by centrifugation.

The successive peroxidation phase cannot even be carried out, for instance in the conditions of EP patent 490,409.

We claim:

1. Purification process of imido-alkancarboxylic acids from contaminants represented by carboxylic acid, lactam or aminoacids and water comprising:

A) preparation of the imido-alkancarboxylic acid by reaction of:

a1) an anhydride of formula

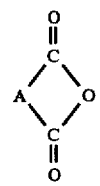

or the corresponding acids, with b1) an aminoacid of formula

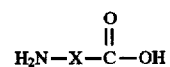

with c1) water; or a1) with b2) a lactam of general formula

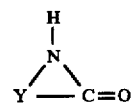

with c1) water; at temperatures comprised betweeen 100° C. and 250° C., under pressure of an inert gas from 1 to 30 bar, for reaction times from 2 to 20 hours;

wherein A indicates a group of formula

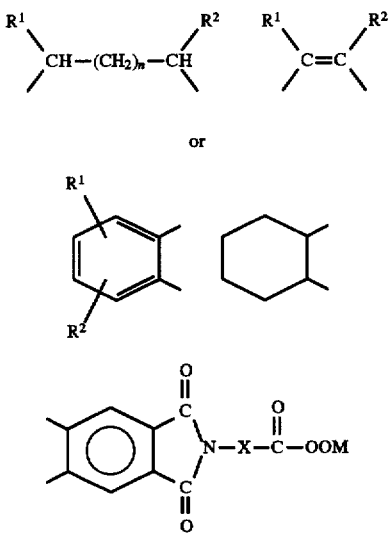

n is an integer 0, 1 or 2,
$R^1$ is hydrogen, chlorine, bromine, alkyl $C_1$–$C_{20}$, alkenyl $C_2$–$C_{20}$, aryl or alkylaryl,
$R^2$ is hydrogen, chlorine, bromine or a group of formula —$SO_3M$, —$CO_2M$, —$CO_3M$, —$OSO_3M$,
M indicates hydrogen, an alkaline metal or ammonium ion or the equivalent of an alkaline-earth metal ion and X indicates alkylene $C_1$–$C_{19}$ or arylene;
Y=X wherein the ratio by moles between a1/(b1 or b2)/c1 is comprised between 1/1.0–1.2/0.5–3;
B) discharge of precursor obtained in phase A) in a solvent immiscible with water;
C) separation of aqueous phases from an organic phase;
D) recovery of the organic phase for the successive peroxidation reaction.

2. Purification process of imido-alkancarboxylic acids according to claim 1 wherein the ratio by moles a1/(b1 or b2)/C1 is comprised between 1/1.05–1.1/0.5–2.5.

3. Purification process of imido-alkancarboxylic acids according to claim 2 wherein the ratio by moles a1/(b1 or b2)/c1) is comprised betwwen 1/1.05–1.1/1–2.

4. Purification process of imido-alkancarboxylic acids according to claim 1 wherein the compounds of the type b) are those of class b2), the compounds of class a1) are selected from the following anhydrides or the corresponding acids: succinic, glutaric, maleic, trimellitic, phthalic, pyromellitic and alkyl- or alkenyl-succinic anhydride; the compounds of the class b1) are selected from: omega-aminobutyric acid, omega-aminovalerianic, omega-aminocaproic and omega-aminolauric acid; the compounds of class b2) are selected from: gamma-pyrrolidone, delta-piperidone, epsilon-caprolactam and omega-laurolactam.

5. Purification process of imido-alkancarboxylic acids according to claim 4 wherein the compound a1) is selected from phthalic anhydride or pthalic acid and the compound b2) is epsilon-caprolactam (CPL).

6. Purification process of imido-alkancarboxylic acids according to claim 1, wherein in phase A) the temperature is comprised between 130° C. and 180° C. and the pressure between 4 and 8 bar.

7. Purification process of imido-alkancarboxylic acids according to claim 1, wherein in phase B) a solvent immiscible with water is employed.

8. Purification process of imido-alkancarboxylic acids according to claim 7, wherein in phase B) the solvent is selected from $CH_2Cl_2$ and $CHCl_3$.

9. Purification process of imido-alkancarboxylic acids according to claim 1, wherein in reaction A) it is operated with an amount of water equal to at least 2 moles per mole of the compound a1).

10. Purification process of imido-alkancarboxylic acids according to claim 9, wherein the melt of the reaction A) is discharged in a solvent of phase B) at temperatures from 78° to 95° C.

11. Purification process of imido-alkancarboxylic acids according to claim 1, wherein in phase A) it is operated with an amount of water lower than 2 moles per mole of the compound a1) and water is added at the end of phase A up to a total amount of at least 2 moles per 1 mole of the compound a1).

12. Process for preparing peroxycarboxylic acids in the presence of hydrogen peroxide and a strong acid wherein the imido-alkancarboxylic acid obtained according to claim 1 is utilized as a precursor.

13. Purification process of imido-alkancarboxylic acids according to claim 1, wherein Y is an alkylene $C_3$–$C_{19}$.

* * * * *